(12) United States Patent
Lee

(10) Patent No.: US 8,328,838 B2
(45) Date of Patent: Dec. 11, 2012

(54) NEEDLE ASSEMBLY FOR TRADITIONAL ORIENTAL MEDICINE

(76) Inventor: Hong-Jae Lee, Seoul (KR)

( * ) Notice: Subject to any disclaimer, the term of this patent is extended or adjusted under 35 U.S.C. 154(b) by 72 days.

(21) Appl. No.: 12/675,787

(22) PCT Filed: Sep. 3, 2008

(86) PCT No.: PCT/KR2008/005166
§ 371 (c)(1),
(2), (4) Date: Mar. 1, 2010

(87) PCT Pub. No.: WO2009/031803
PCT Pub. Date: Mar. 12, 2009

(65) Prior Publication Data
US 2010/0256664 A1    Oct. 7, 2010

(30) Foreign Application Priority Data

Sep. 3, 2007   (KR) .................. 10-2007-0088771

(51) Int. Cl.
*A61B 17/34*   (2006.01)
(52) U.S. Cl. ...................................... 606/189
(58) Field of Classification Search .................. 606/181, 606/182, 189; 604/192, 263
See application file for complete search history.

(56) References Cited

U.S. PATENT DOCUMENTS

| 5,089,001 | A | * | 2/1992 | Hwang | .......... | 606/189 |
| 2005/0267507 | A1 | * | 12/2005 | Kao | .............. | 606/189 |

FOREIGN PATENT DOCUMENTS

| KR | 1990-0004959 | 6/1990 |
| KR | 20-0250442 | 10/2001 |
| KR | 20-0296733 | 11/2002 |

* cited by examiner

*Primary Examiner* — Tuan V Nguyen
(74) *Attorney, Agent, or Firm* — Ladas & Parry LLP

(57) ABSTRACT

Provided is a needle assembly for use in oriental acupuncture. The needle assembly includes: a hollow tubular rod member; a pin member which is movably installed in the rod member and can be inserted into a person's skin; and a reuse preventing unit preventing the pin member, which is protruded from an end of the rod member and is inserted into the skin, from being protruded from the end of the rod member and inserted into the skin again.

9 Claims, 9 Drawing Sheets

NEEDLE ASSEMBLY FOR TRADITIONAL ORIENTAL MEDICINE

TECHNICAL FIELD

The present invention relates to a needle assembly for use in oriental acupuncture, and more particularly, to a needle assembly for use in oriental acupuncture which can prevent a needle from contacting the skin or an external object.

BACKGROUND ART

FIG. 1 is a cross-sectional view of a conventional needle assembly for use in oriental acupuncture. Referring to FIG. 1, the needle assembly includes a tubular rod member A and a pin member B which is movably installed in the rod member A and can be inserted into the skin S.

In the state where the pin member B is inserted into the rod member A, the conventional needle assembly is sealed and packed.

The conventional needle assembly for use in oriental acupuncture, which is constructed as described above, has the following disadvantages.

In order to perform acupuncture by using the pin number B, the conventional needle assembly is unpacked first. Next, the rod member A is held in the hand and the pin member B is brought into contact with the skin S. Next, an upper end of the pin member B is pressed so that the pin member B is inserted into the skin S.

However, since the pin member B is movably installed in the rod member A, if the rod member A is even slightly oblique to a parallel line P as shown in FIG. 2, the pin member B is abruptly removed from the rod member A.

Accordingly, an operator should be very careful to prevent the pin member B from being removed from the rod member A until the pin member B contacts a patient's body. Despite the operator's care, the pin member B often fails to be placed at a correct acupuncture point on the patient's body due to the mobility of the pin member B.

Meanwhile, as shown in FIG. 3, the operator generally performs acupuncture while stopping the movement of a lower end of the pin member B with his or her fingers in order to prevent the removal of the pin member B from the rod member A. Accordingly, if the operator's fingers are infected, the patient may also be infected due to the pin member B that is in contact with the infected fingers. Furthermore, the pin member B should be thrown away after use. However, the pin member B is sometimes used again after sterilization. Accordingly, there is a demand for technology for preventing the reuse of the pin member B.

DETAILED DESCRIPTION OF THE INVENTION

Technical Problem

The present invention provides a needle assembly for use in oriental acupuncture, which can prevent infection during acupuncture.

The present invention also provides a needle assembly for use in oriental acupuncture, which can prevent the reuse of a pin member.

Technical Solution

According to an aspect of the present invention, there is provided a needle assembly for use in oriental acupuncture, the needle assembly comprising: a hollow tubular rod member; a pin member movably installed in the rod member and inserted into a person's skin; and a reuse preventing unit preventing the pin member, which is protruded from an end of the rod member and inserted into the skin, from being protruded from the end of the rod member and inserted into the skin again.

The rod member may comprise: a tube part having a long through-hole; and an accommodating part surrounding an outer circumferential surface of the tube part and having an accommodating space defined by an inner circumferential surface of the accommodating part and a surface of an end of the tube part, wherein the reuse preventing unit comprises an insertion block disposed in the accommodating space, wherein the insertion block comprises: an insertion part having a hole into which the pin member is inserted; and a central part extending from the insertion part, and adapted to be deviated from an axis which the pin member follows in the state where the pin member is inserted into the hole of the insertion part and to be aligned with the axis when the pin member is removed from the hole of the insertion part.

The rod member may comprise: a tube member having a long through-hole; and an accommodating part surrounding an outer circumferential surface of the tube member and having an accommodating space defined by an inner circumferential surface of the accommodating part and a surface of an end of the tube part, wherein the reuse preventing unit comprises a protrusion part having a through-hole whose central line is aligned with a central axis of the rod member and extending from the accommodating part to taper from a lower end toward an upper end of the rod member, wherein the pin member is inserted into the skin in the state where the pin member is inserted into the through-hole of the protrusion part, and when the pin member is removed from the through-hole of the protrusion part, an end of the pin member is deviated from the central axis of the rod member.

The reuse preventing unit may comprise an insertion part having a through-hole whose central line is aligned with a central axis of the rod member and allows the pin member to be inserted thereinto, and tapering from a lower end toward an upper end of the rod member, wherein the pin member is inserted into the skin in the state where the pin member is inserted into the through-hole of the insertion part, and when the pin member is removed from the through-hole of the insertion part, an end the pin member is deviated from the central axis of the rod member.

The needle assembly may further comprise a movement restraining unit restraining the movement of the pin member relative to the rod member in the state where the pin member is inserted into the rod member.

The needle assembly may further comprise a pressing member coupled to the pin member to be moved relative to the rod member along with the pin member, wherein the movement restraining unit comprises: a first projection formed on an outer circumferential surface of the pressing member; a second projection formed on the outer circumferential surface of the pressing member to be spaced apart from the first projection; and a position fixing protrusion formed on an inner circumferential surface of the rod member and inserted between the first projection and the second projection.

The movement restraining unit may further comprise a first stopper holding the first projection of the pressing member and a second stopper holding the second projection of the pressing member in order to prevent the pressing member and the pin member from being separated from the rod member when the pressing member is removed from between the first projection and the second projection of the first stopper and is moved relative to the rod member.

MODE OF THE INVENTION

The present invention will now be described more fully with reference to the accompanying drawings, in which exemplary embodiments of the invention are shown.

Figure 1:
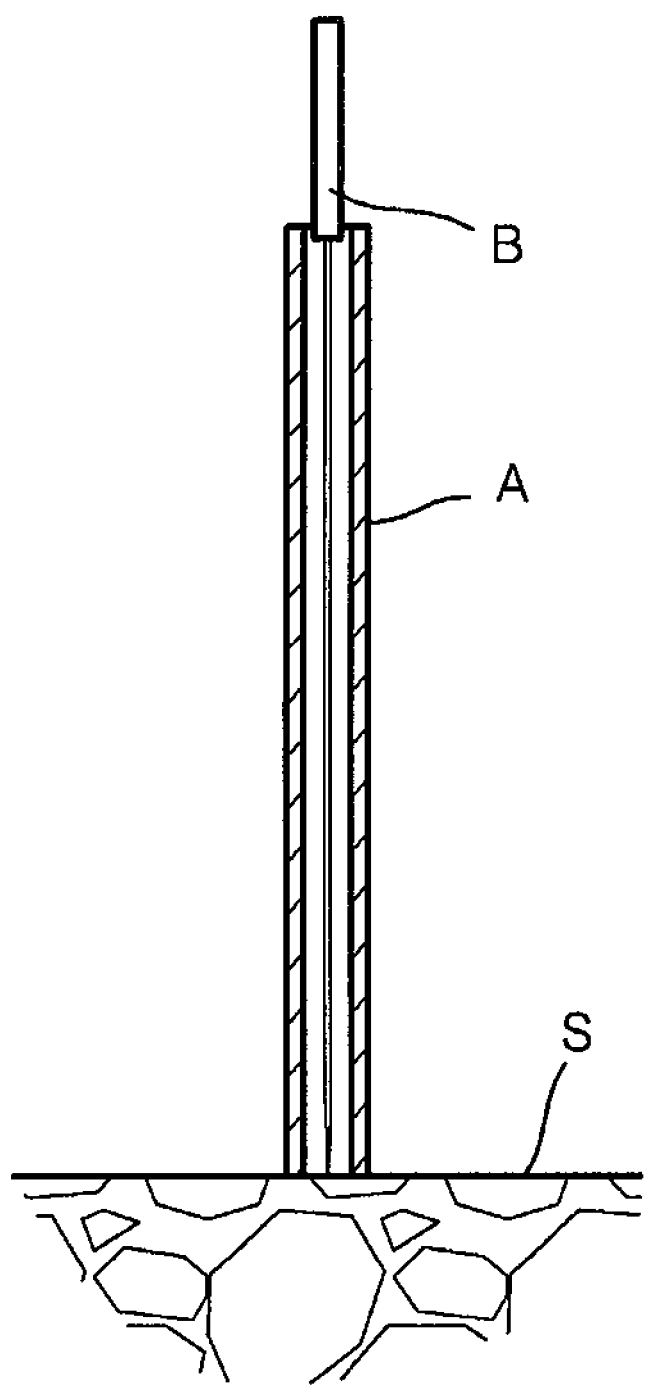
FIG. 1 is a cross-sectional view of a conventional needle assembly for use in oriental acupuncture.
Figure 2:
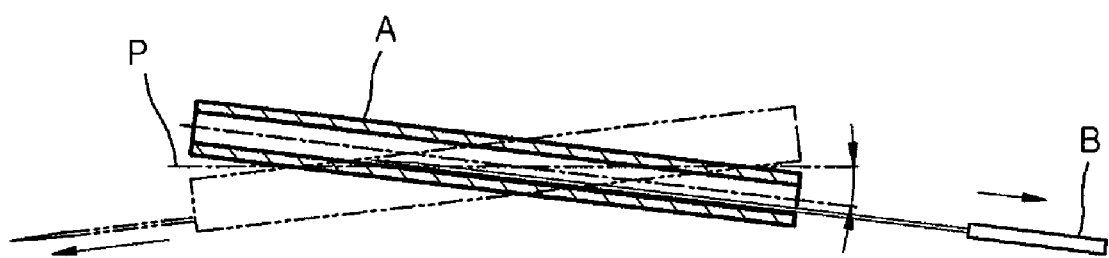
FIGS. 2 and 3 are cross-sectional views for explaining the disadvantages of the conventional needle assembly of FIG. 1.
Figure 3:
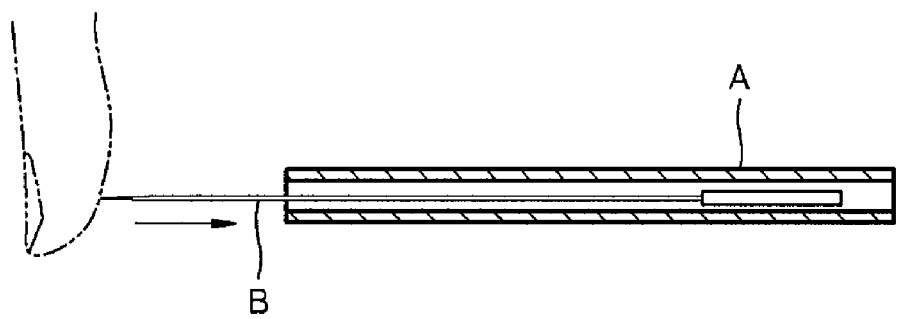
Figure 4:
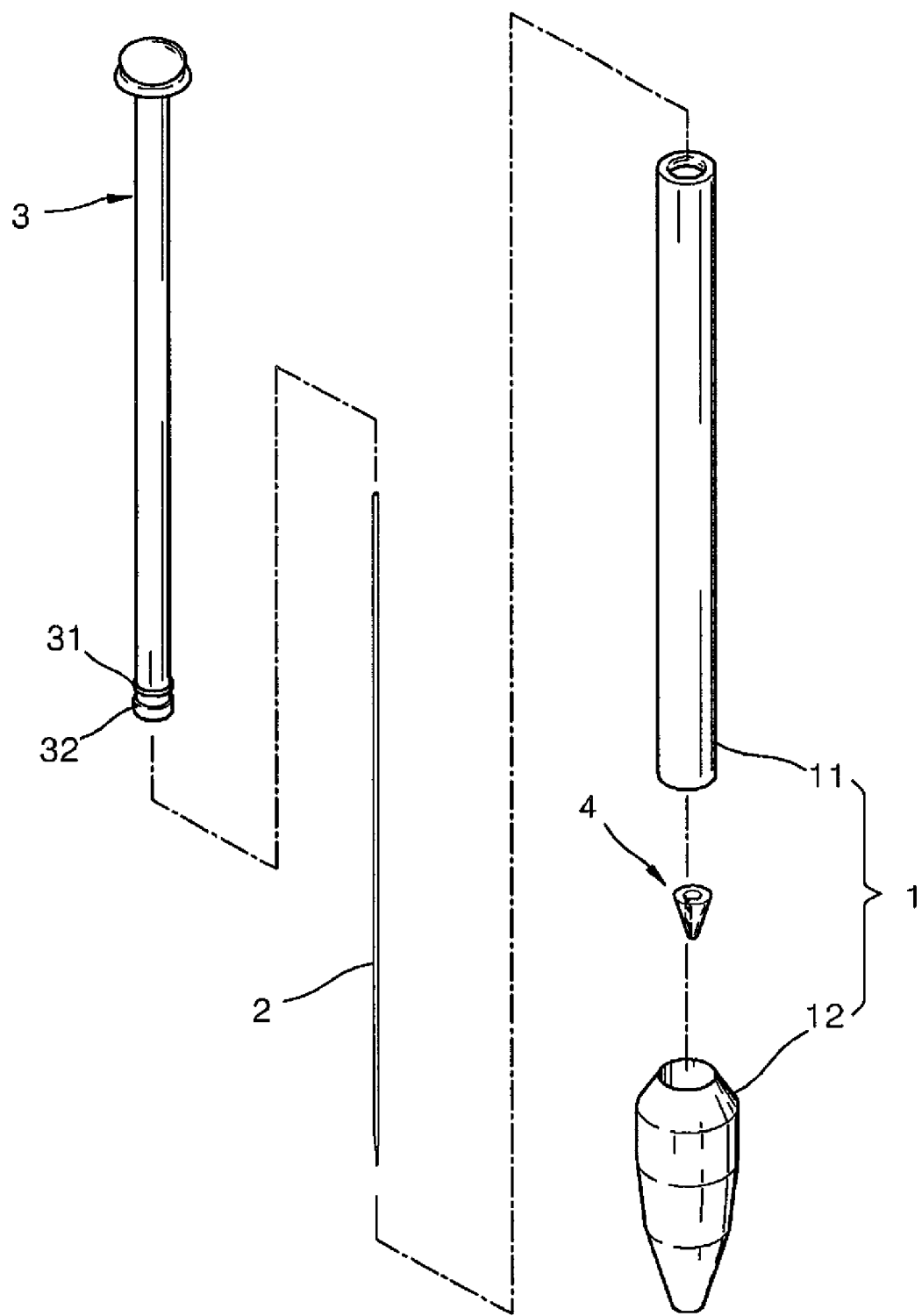
FIG. 4 is an exploded perspective view of a needle assembly for use in oriental acupuncture according to an embodiment of the present invention.
Figure 5:
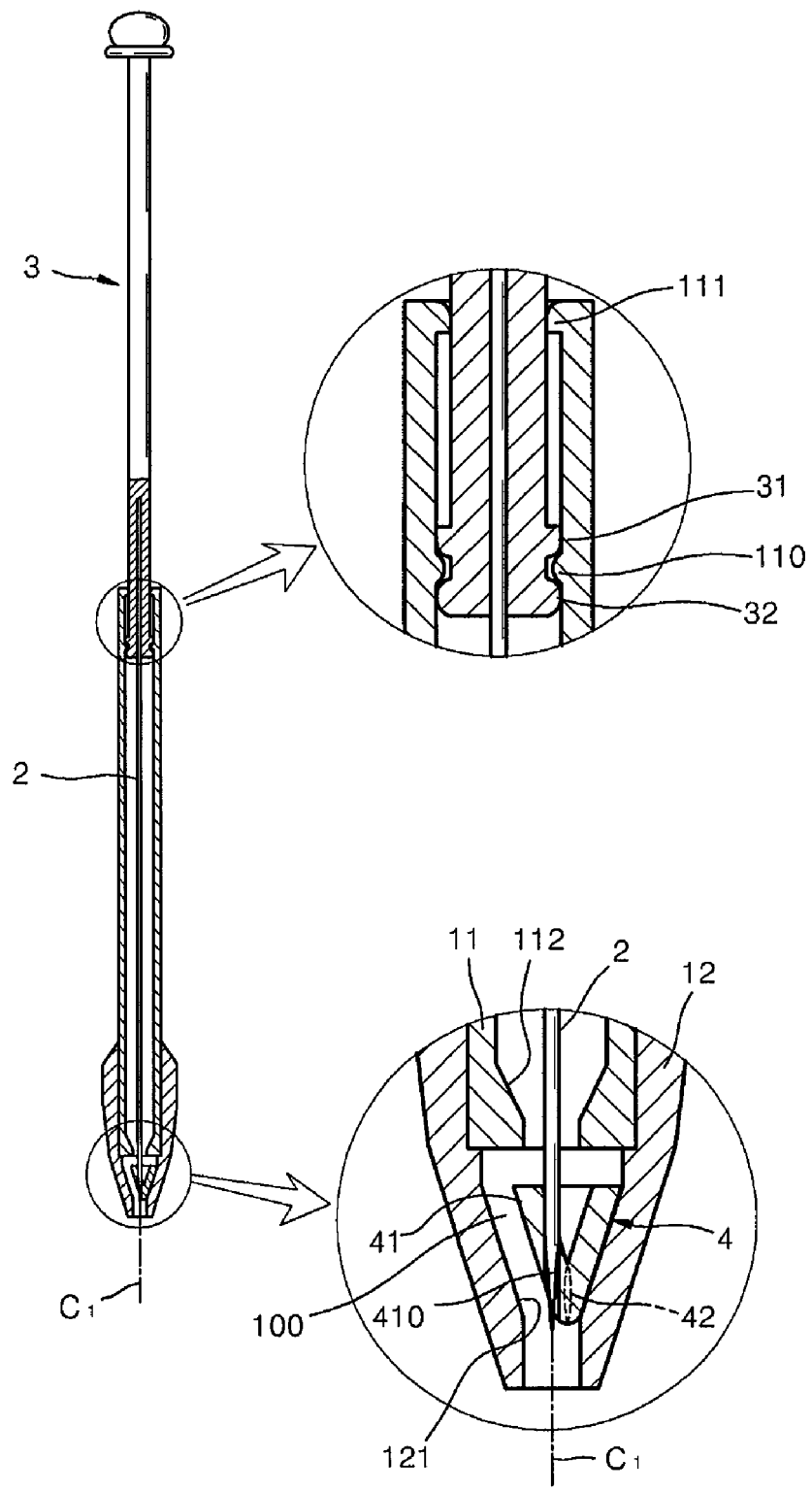
FIG. 5 is a cross-sectional view of the needle assembly of FIG. 4.

FIG. 4 is an exploded perspective view of a needle assembly for use in oriental acupuncture according to an embodiment of the present invention. FIG. 5 is a cross-sectional view of the needle assembly of FIG. 4.

Referring to FIGS. 4 and 5, the needle assembly, which can be inserted into a point on a person's body with the aim of relieving pain or for therapeutic purposes, includes a hollow tubular rod member 1, a pin member 2 which is movably installed in the rod member 1 and can be inserted into the skin S of a person, and a reuse preventing unit preventing reuse of the pin member 2 that has already been used once.

The reuse preventing unit prevents the pin member 2, which is protruded from an end of the rod member 1 and inserted into the skin S, from being protruded from the end of the rod member 1 and inserted into the skin S again, and includes an insertion block 4 that is disposed in an accommodating space 100 of an accommodating part 12.

That is, the rod member 1 includes a tube part 11 having a long through-hole, and the accommodating part 12 surrounding an outer circumferential surface of the tube part 11. The accommodating part 12 includes the accommodating space 100 defined by an inner circumferential surface of the accommodating part 12 and a surface of the end of the tube part 11.

The insertion block 4 includes an insertion part 41 and a central part 42. The insertion part 41 has a hole 410 into which the pin member 2 is inserted. The central part 42 is deviated from an axis $C_1$ which the pin member 2 follows in the state where the pin member 2 is inserted into the hole 410 of the insertion part 41. The central part 42 is aligned with the axis $C_1$ when the pin member 2 is removed from the hole 410.

Figure 6:
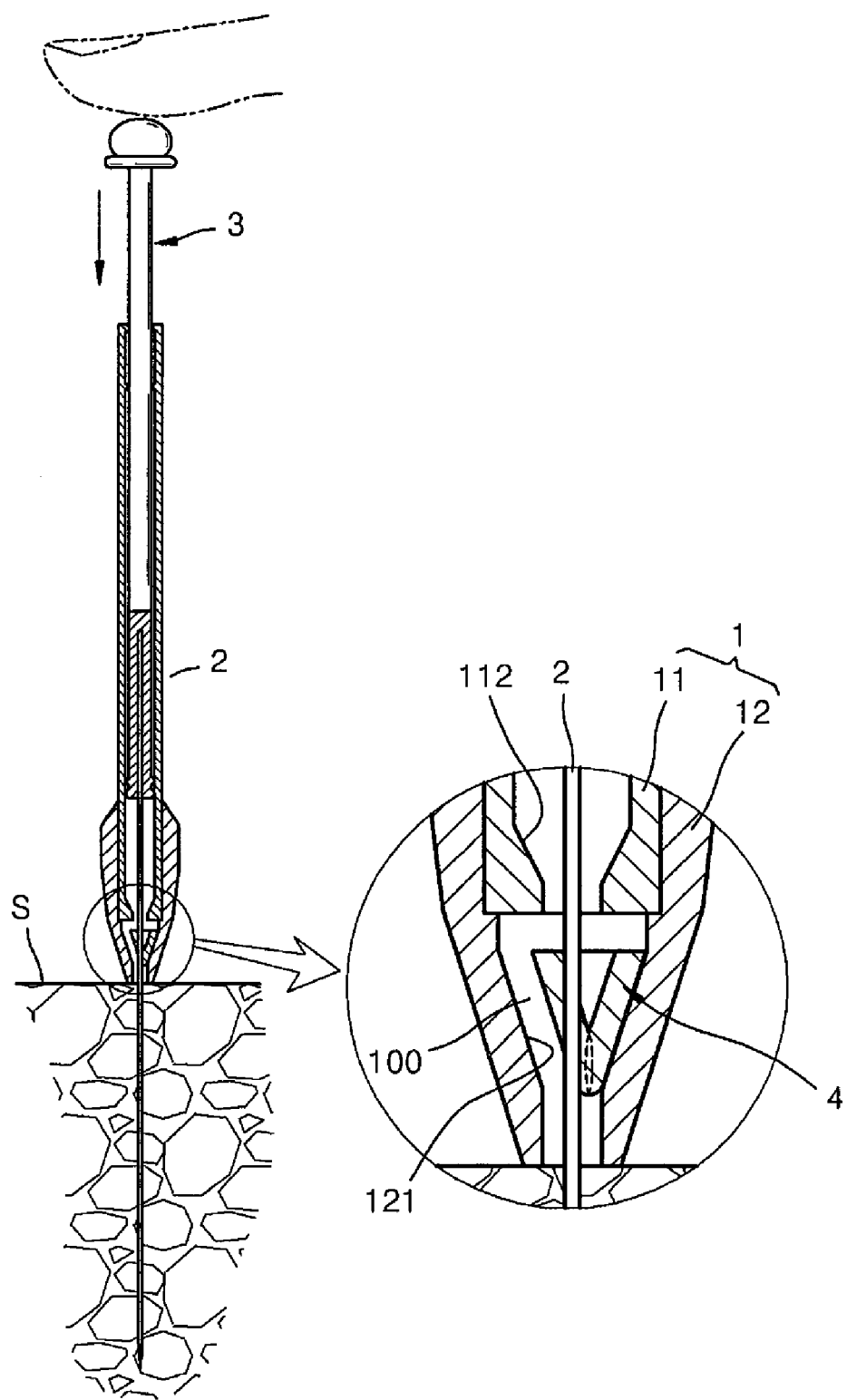
FIG. 6 is a cross-sectional view illustrating the needle assembly of FIG. 4 being used.
Figure 7:
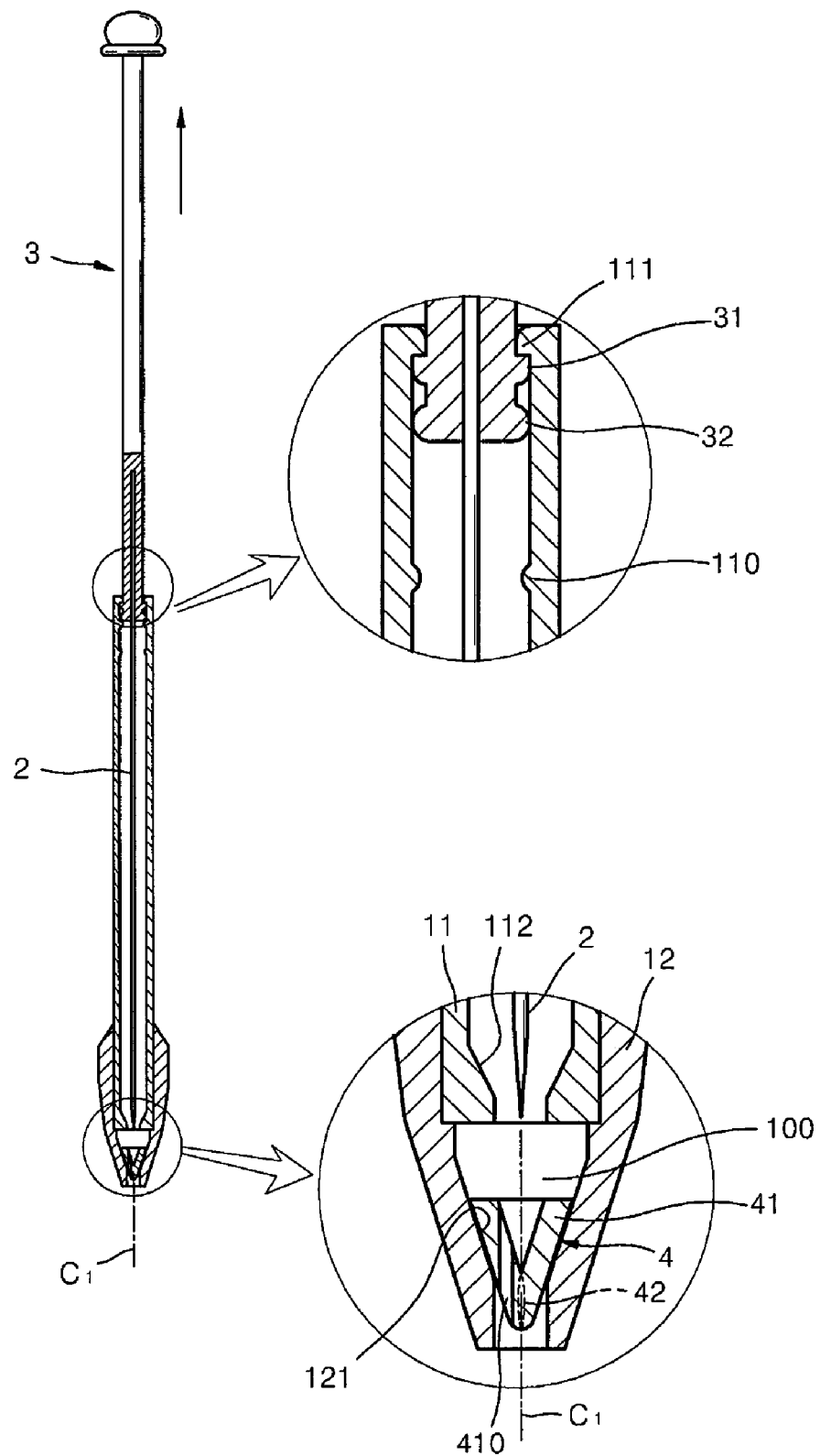
FIG. 7 is a cross-sectional view illustrating the needle assembly of FIG. 4 being operated.
Figure 8:
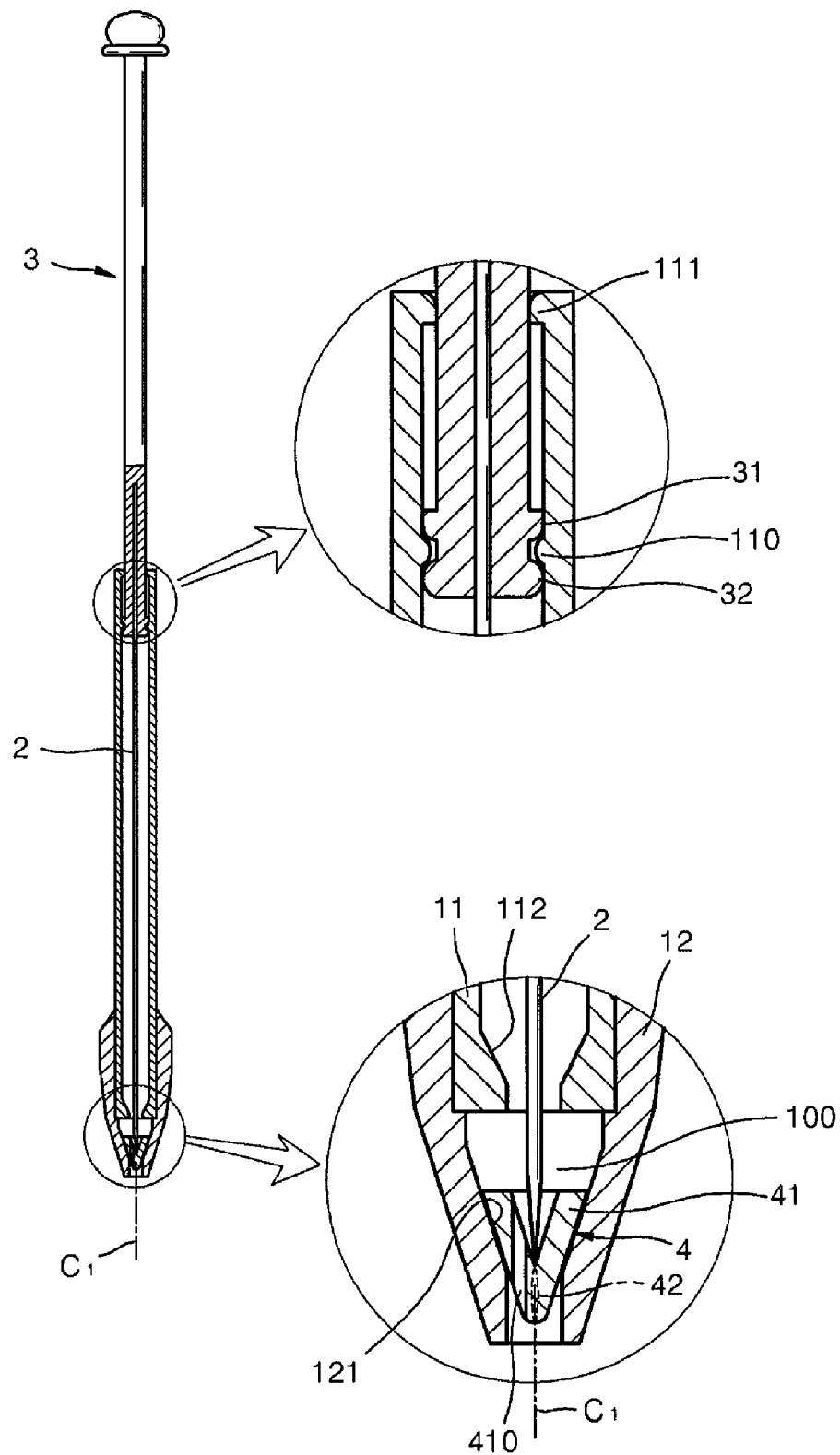
FIG. 8 is a cross-sectional view for explaining the advantages of the needle assembly of FIG. 4.

Since the needle assembly of FIG. 4 includes the reuse preventing unit, after acupuncture is carried out as shown in FIG. 6, if the pin member 2, which is removed from the hole 410 of the insertion part 41, is again forcefully inserted into the hole 410 of the insertion part 41 as shown in FIG. 8, the pin member 2 is caught by the central part 42 that is aligned with the axis $C_1$ and thus the pin member 2 is prevented from being inserted into the insertion part 41, thereby preventing the pin member 2 from being exposed to the outside of the rod member 1. As a result, the pin member 2, which is used for acupuncture once, can be prevented from being used again. Meantime, the accommodating part 12 may have a tapered surface 121 whose inner diameter decreases toward an end of the accommodating part 12. The tapered surface 121 guides the central part 42 of the insertion block 4 to a position where the central part 42 is aligned with the axis $C_1$, when the pin member 2 is removed from the hole 410 of the insertion part 41.

The needle assembly of FIG. 4 further includes a movement restraining unit restraining the movement of the pin member 2 in order to fix the pin member 2 to the rod member 1.

The needle assembly of FIG. 4 further includes a pressing member 3 coupled to the pin member 2. The pressing member 3 is movably installed in the rod member 1 along with the pin member 2. The pressing member 3 is formed of a material such as synthetic resin. The pin member 2 is formed of a material such as aluminium, titanium, stainless steel, silver, or gold.

The movement restraining unit restrains the pin member 2 from being moved relative to the rod member 1 in the state where the pin member 2 is inserted into the rod member 1, and includes a first projection 31, a second projection 32, and a position fixing protrusion 110. The first projection 31 is formed on an outer circumferential surface of the pressing member 3 and is moved across the position fixing protrusion 110 if the pressing member 3 is pressed. The second projection 32 is formed on the outer circumferential surface of the pressing member 3 to be spaced apart from the first projection 31.

The position fixing protrusion 110 fixes the pin member 2 and the pressing member 3 to the rod member 1 by being inserted between the first projection 31 and the second projection 32. Once an external pressing force is applied to the pressing member 3, the position fixing protrusion 110 is removed from between the first and second projections 31 and 32 such that the pin member 2 and the pressing member 3 can be moved relative to the rod member 1.

Since the needle assembly of FIG. 4 includes the movement restraining unit, an operator can perform acupuncture in a more sanitary and convenient manner. That is, since the pin member 2 is fixed to the rod member 1 by the movement restraining unit until the pin member 2 contacts a patient's body, the operator can locate the pin member 2 at a correct acupuncture spot without contacting his/her fingers with the pin member 2.

The movement restraining unit may include a first stopper 111 and a second stopper 112. The first stopper 111 holds the first projection 31 of the pressing member 3 in order to prevent the pin member 2 from being completely separated from the rod member 1 in a direction opposite to a direction in which the pin member 2 is moved toward the skin S.

The second stopper 112 holds the second projection 32 of the pressing member 3 when the first stopper 111 is removed from between the first projection 31 and the second projection 32 and the pressing member 3 is moved relative to the rod member 1. The second stopper 112 prevents the pin member 2 from being completely separated from the rod member 1 in the direction in which the pin member 2 is moved toward the skin S.

Since the needle assembly of FIG. 4 includes the first stopper 111 and the second stopper 112, the pin member 2 can be prevented from being separated from the rod member 1, thereby preventing the reuse of the pin member 2 that has been used once.

Figure 9:
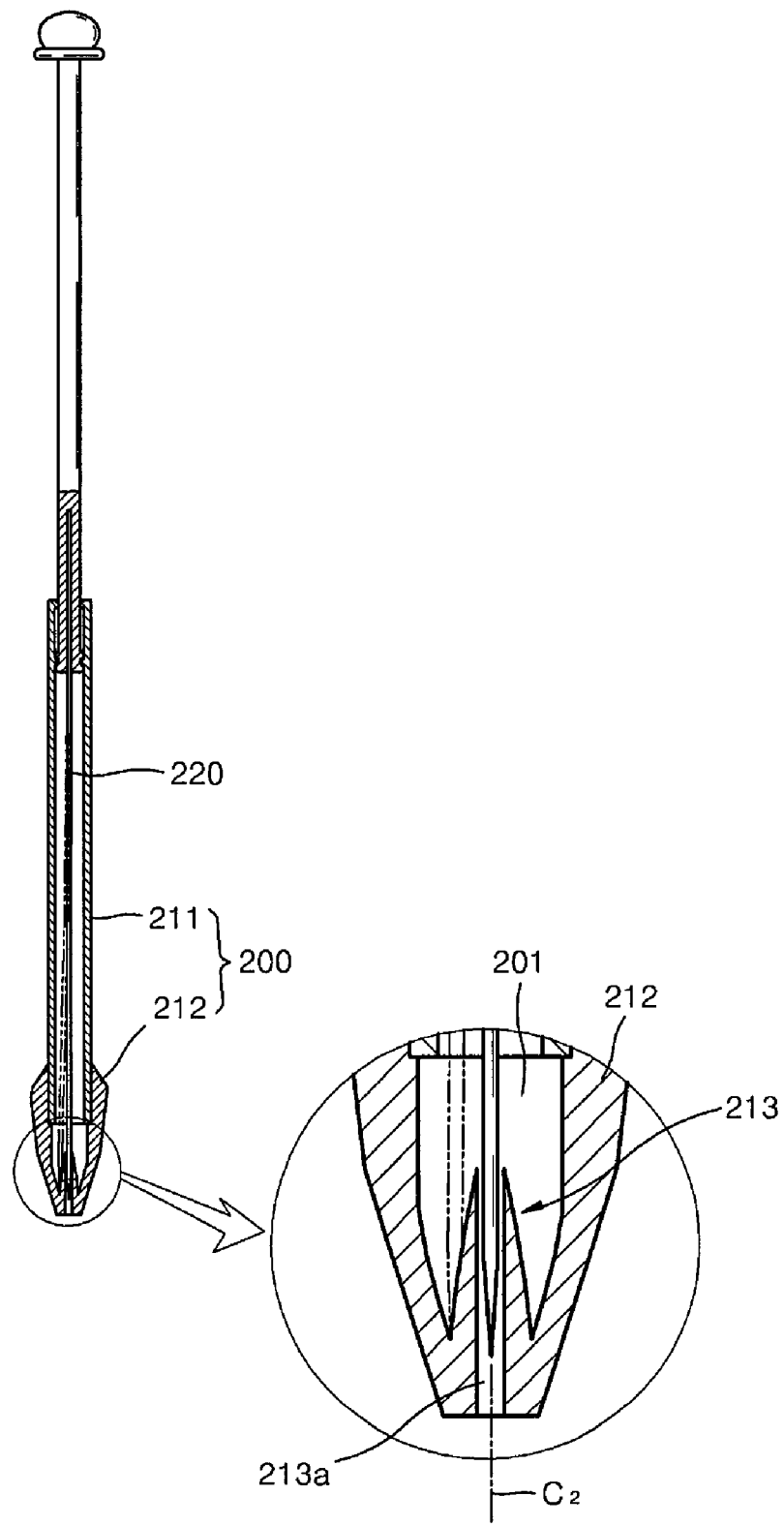
FIG. 9 is a cross-sectional view of a needle assembly for use in oriental acupuncture according to another embodiment of the present invention.

FIG. 9 is a cross-sectional view of a needle assembly for use in oriental acupuncture according to another embodiment of the present invention. A rod member 200 includes a tube part 211 having a long through-hole, and an accommodating part 212 surrounding an outer circumferential surface of the tube part 211 and having an accommodating space 201 defined by an inner circumferential surface of the accommodating part 212 and a surface of an end of the tube part 211.

A reuse preventing unit of the needle assembly of FIG. 9 includes a protrusion part 213 having a through-hole 213a whose central line is aligned with a central axis $C_2$ of the rod member 200, and extending from the accommodating part 212 to taper from a lower end toward an upper end of the rod member 200.

A pin member 220 is inserted into a person's skin in the state where the pin member 220 is inserted into the through-hole 213a of the protrusion part 213 as shown by a dash-dot-dash line of FIG. 9, and when the pin member 220 is removed from the through-hole 213a of the protrusion part 213, an end of the pin member 220 is deviated from the central axis $C_2$ of the rod member 200 as shown by a dash-dot-dot-dash line of FIG. 9. Accordingly, since the pin member 220 that is used once is deviated from the central axis $C_2$ of the protrusion part 213 and is caught by an outer surface of the protrusion part 213, reuse of the pin member 220 can be prevented.

Figure 10:
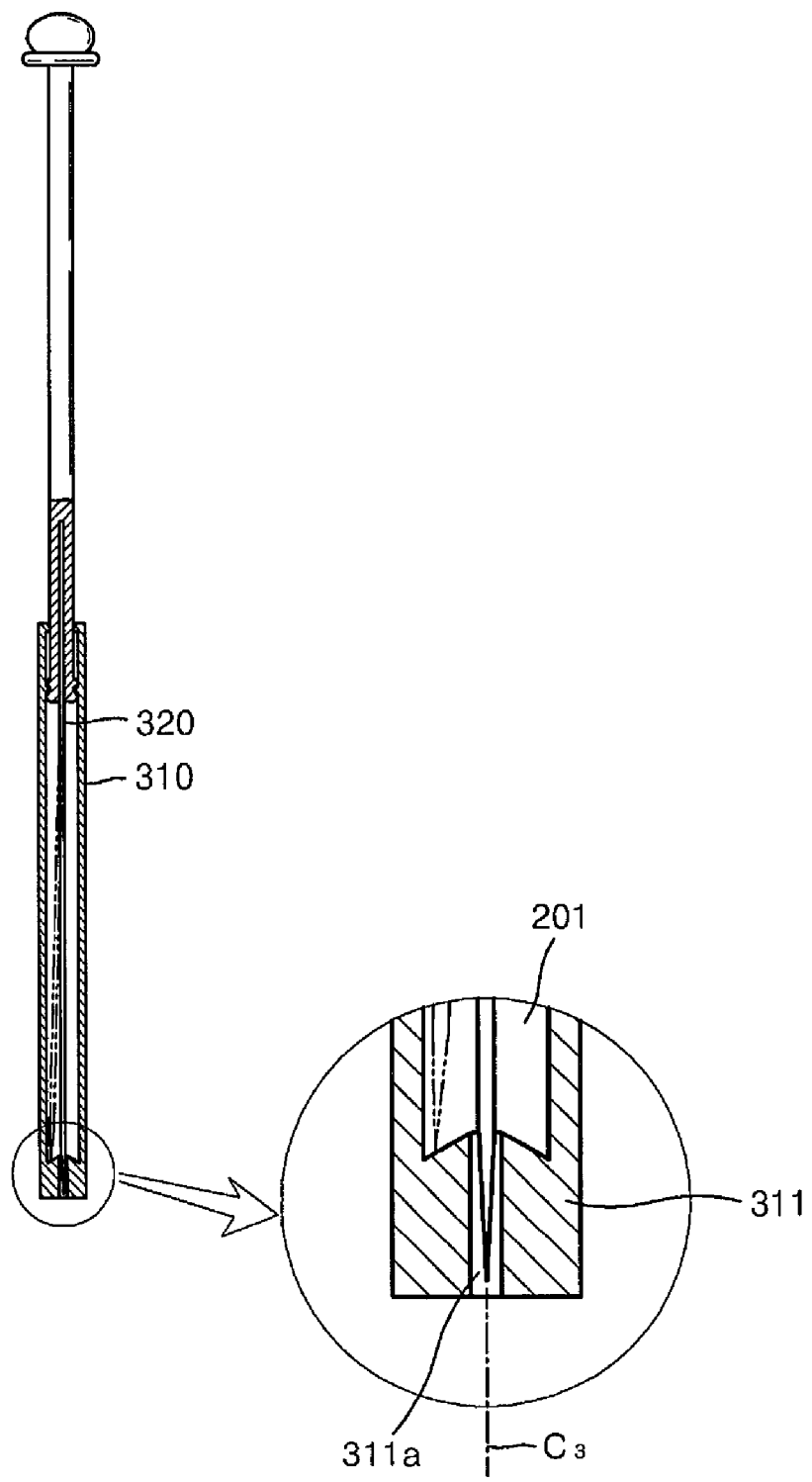
FIG. 10 is a cross-sectional view of a needle assembly for use in oriental acupuncture according to another embodiment of the present invention.

FIG. 10 is a cross-sectional view of a needle assembly for use in oriental acupuncture according to another embodiment of the present invention. Referring to FIG. 10, a reuse preventing unit includes an insertion part 311 having a through-hole 311a whose central line is aligned with a central axis $C_3$ of a rod member 310, allowing a pin member 320 to be inserted thereinto, and tapering from a lower end toward an upper end of the rod member 310.

The pin member 320 is inserted into a person's skin in the state where the pin member 320 is inserted into the through-hole 311a of the insertion part 311 as shown by a dash-dot-dash line of FIG. 10, and when the pin member 320 is removed from the through-hole 311a of the insertion part 311, an end of the pin member 320 is deviated from the central axis $C_3$ of the rod member 310 as shown by a dash-dot-dot-dash line of FIG. 10. Accordingly, like in FIG. 9, since the pin member 320 that is used once is deviated from the central axis $C_3$ of the rod member 310 and is caught by an outer surface of the insertion part 311, reuse of the pin member 320 can be prevented.

While the present invention has been particularly shown and described with reference to exemplary embodiments thereof, it will be understood by those of ordinary skill in the art that various changes in form and details may be made therein without departing from the spirit and scope of the present invention as defined by the following claims.

INDUSTRIAL APPLICABILITY

As described above, since the needle assembly for use in oriental acupuncture according to the present invention includes the reuse preventing unit that can prevent reuse of the pin member, the pin member that is used once can be prevented from being used again.

Since the needle assembly according to the present invention includes the movement restraining unit that can restraint the movement of the pin member relative to the rod member, the pin member can be prevented from being infected due to an operator's infected fingers, and the needle part can be more easily and conveniently inserted into a desired acupuncture point.

The invention claimed is:

1. A needle assembly for use in oriental acupuncture, the needle assembly comprising:
    a hollow tubular rod member;
    a pin member movably installed in the rod member and capable of being inserted into a person's skin; and
    a reuse preventing unit preventing the pin member, which is protruded from a distal end of the hollow tubular rod member and inserted into the skin, from being protruded from the distal end of the hollow tubular rod member and from being inserted into the skin again after the pin is withdrawn from the skin,
    wherein the hollow tubular rod member comprises:
        a tube part having a long through-hole; and
        an accommodating part surrounding an outer circumferential surface of the tube part and having an accommodating space defined by an inner circumferential surface of the accommodating part and a surface of an end of the tube part,
    wherein the reuse preventing unit comprises an insertion block disposed in the accommodating space, wherein the insertion block comprises:
        an insertion part having a hole into which the pin member is inserted; and
        a central part extending from the insertion part, and adapted to be deviated from an axis which the pin member follows in the state where the pin member is inserted into the hole of the insertion part and to be aligned with the axis when the pin member is removed from the hole of the insertion part.

2. The needle assembly of claim 1, wherein t the hole of the insertion part has a central line that is aligned with a central axis of the tube part to allow the pin member to be inserted thereinto, and tapering from a lower end toward an upper end of the tube part.

3. The needle assembly of claim 1, further comprising a movement restraining unit restraining the movement of the pin member relative to the tube member in the state where the pin member is inserted into the tube member.

4. The needle assembly of claim 3, further comprising a pressing member coupled to the pin member to be moved relative to the tube member along with the pin member,
    wherein the movement restraining unit comprises:
        a first projection formed on an outer circumferential surface of the pressing member;
        a second projection formed on the outer circumferential surface of the pressing member to be spaced apart from the first projection; and
        a position fixing protrusion formed on an inner circumferential surface of the rod member and inserted between the first projection and the second projection.

5. The needle assembly of claim 4, wherein the movement restraining unit further comprises a first stopper holding the first projection of the pressing member and a second stopper holding the second projection of the pressing member in order to prevent the pressing member and the pin member from being separated from the tube member when the pressing member is removed from between the first projection and the second projection of the first stopper and is moved relative to the tube member.

6. A needle assembly for use in oriental acupuncture, the needle assembly comprising:
    a hollow tubular rod member;

a pin member movably installed in the rod member and capable of being inserted into a person's skin; and a reuse preventing unit preventing the pin member, which is protruded from a distal end of the hollow tubular rod member and inserted into the skin, from being protruded from the distal end of the hollow tubular rod member and from being inserted into the skin again after the pin is withdrawn from the skin, wherein the hollow tubular rod member comprises:

a tube member having a long through-hole; and an accommodating part surrounding an outer circumferential surface of the tube member and having an accommodating space defined by an inner circumferential surface of the accommodating part and a surface of an end of the tube part, wherein the reuse preventing unit comprises a protrusion part having a through-hole whose central line is aligned with a central axis of the tube member and extending from the accommodating part to taper from a lower end toward an upper end of the tube member, wherein the pin member is capable of being inserted into the skin in the state where the pin member is inserted into the through-hole of the protrusion part, and when the pin member is removed from the through-hole of the protrusion part, an end of the pin member is deviated from the central axis of the tube member.

7. The needle assembly of claim 6, further comprising a movement restraining unit restraining the movement of the pin member relative to the tube member in the state where the pin member is inserted into the tube member.

8. The needle assembly of claim 7, further comprising a pressing member coupled to the pin member to be moved relative to the tube member along with the pin member, wherein the movement restraining unit comprises:

a first projection formed on an outer circumferential surface of the pressing member;

a second projection formed on the outer circumferential surface of the pressing member to be spaced apart from the first projection; and a position fixing protrusion formed on an inner circumferential surface of the tube member and inserted between the first projection and the second projection.

9. The needle assembly of claim 8, wherein the movement restraining unit further comprises a first stopper holding the first projection of the pressing member and a second stopper holding the second projection of the pressing member in order to prevent the pressing member and the pin member from being separated from the tube member when the pressing member is removed from between the first projection and the second projection of the first stopper and is moved relative to the tube member.

\* \* \* \* \*